United States Patent [19]

Miller et al.

[11] Patent Number: 4,904,249
[45] Date of Patent: Feb. 27, 1990

[54] ABSORBENT UNDERGARMENT WITH FLUID TRANSFER LAYER AND ELASTICIZED CROTCH DESIGN

[75] Inventors: Peggy H. Miller, Kimberly; Gary D. Winters, Appleton, both of Wis.

[73] Assignee: Kimberly-Clark Corporation, Neenah, Wis.

[21] Appl. No.: 203,222

[22] Filed: Jun. 6, 1988

[51] Int. Cl.$^4$ ............................................. A61F 13/16
[52] U.S. Cl. ................................... 604/378; 428/152; 428/283; 428/284; 428/913; 604/358; 604/367; 604/385.1
[58] Field of Search ............... 428/284, 913, 283, 152; 604/358, 367, 378, 385.1

[56] References Cited

U.S. PATENT DOCUMENTS

| | | | |
|---|---|---|---|
| 32,649 | 4/1888 | Brandt et al. | 604/368 |
| 4,050,462 | 9/1977 | Woon et al. | 128/287 |
| 4,315,508 | 2/1982 | Bolick | 128/289 |
| 4,338,371 | 7/1982 | Dawn et al. | 428/283 |
| 4,397,644 | 8/1983 | Matthews et al. | 604/378 |
| 4,480,000 | 10/1984 | Watanabe et al. | 428/284 |
| 4,673,402 | 6/1987 | Weisman et al. | 604/378 |
| 4,685,909 | 8/1987 | Berg et al. | 604/360 |
| 4,699,619 | 10/1987 | Bernardin | 604/378 |
| 4,834,735 | 5/1989 | Alemany et al. | 604/368 |

FOREIGN PATENT DOCUMENTS

| | | |
|---|---|---|
| 5783186 | 5/1985 | Australia . |
| 84106820 | 8/1985 | European Pat. Off. . |
| 2023068 | 12/1979 | United Kingdom . |
| 2101038 | 1/1983 | United Kingdom . |

Primary Examiner—James J. Bell
Attorney, Agent, or Firm—Douglas L. Miller; Thomas J. Mielke; John L. Chiatalas

[57] ABSTRACT

A garment (20) for use in absorbing and containing waste comprising a generally rectangular liquid impervious backing (22) having a peripheral edge (24) and a generally rectangular liquid pervious body-side liner (40) having a peripheral edge (42). The liquid impervious backing (22) and liquid pervious liner (40) are joined at their peripheral edges (24,42) to form a container (74). A generally rectangular absorbent layer (58) is between the liner (40) and the backing (22). A generally rectangular pledget (76), which is made of absorbent material, is positioned between the absorbent layer (58) and the backing (22). The pledget (76) has a width and length less than the width and length of the absorbent layer (58).

25 Claims, 3 Drawing Sheets

ABSORBENT UNDERGARMENT WITH FLUID TRANSFER LAYER AND ELASTICIZED CROTCH DESIGN

BACKGROUND OF THE INVENTION

This invention pertains to an absorbent undergarment, and more particularly, to an absorbent undergarment for effectively containing and absorbing body waste.

Various types of garments are presently available for absorbing human discharge. Examples of these garments include baby diapers, feminine care products, incontinence garments and the like. Generally speaking, the basic structure of this class of garments requires a liquid pervious bodyside liner, an absorbent layer or layers for receiving and absorbing the discharge, and a liquid impervious outer cover or backing for containing the discharge.

While some of these garments perform satisfactorily for their intended purpose, there remains the need to provide an undergarment that possesses improved absorption characteristics, as well as improved waste containment characteristics with a minimum of discomfort to the wearer. More specifically, heretofore, undergarments of this type have not been designed to facilitate the transfer of liquids to the entire area, including the distal ends, of the absorbent layer or layers. As a result, waste absorption is concentrated in the central portion of the absorbent layer which results in an under utilization of much of the absorbent capacity of the undergarment.

Heretofore, some undergarments for absorbing and containing human discharge have typically been bulky and somewhat ineffective. For example, such undergarments may comprise flat sheets folded up into a diaper-like configuration which are bulky, particularly in the crotch portion. Obviously, this style of undergarment is uncomfortable to wear, especially if the wearer is an active adult.

Australian Patent Specification No. 57831/86 to Haire is directed to a diaper having a water pervious facing sheet made of a nonwoven web formed from cellulosic fibers, and a water impervious backing sheet. An absorbent pad, positioned between the facing and the backing sheets, comprises one layer made of a loose batt of wood or paper pulp, generally coextensive with the facing and backing sheets, and second and third narrower layers located essentially along the central axis of the diaper. The third layer, which has a higher absorbency than the other two layers, is sandwiched between the other two absorbent layers. The second layer is centrally positioned since it is said that increased absorbency is required in this area.

U.S. Pat. No. 4,480,000 to Wanatabe et al. is directed to an absorbent article that is of a generally planar configuration. The absorbent article shown in the Watanabe et al. U.S. Pat. No. has a conventional absorbent layer having its lateral faces and underneath face covered by a conventional barrier. A web, or mass of polyester fibers in the form of a sheet of non-interlaced and non-bonded fibers is on top of the absorbent layer. A nonwoven fabric, made of a blend of a regenerated cellulose fiber, a polyester fiber and a heat-bondable polyolefin composite fiber, is wrapped around the absorbent layer, the barrier and the web. The Watanabe et al. U.S. Pat. No. states that an enhanced absorption rate and feeling of dryness are due to the fact that a polyester fiber is contained in both the nonwoven fabric and the web.

European Patent Application No. 84106820.8 to Damico shows an absorbent incontinent garment having a pervious body facing member, an inner lower pad member and an impervious polymer member, which is wrapped around the pad member and adhered to the facing member. The middle portion of the garment contains an additional layer of absorbent, and further has elastic extending along the longitudinal edges of the pad. The contraction of the elastic is said to create a pouch that is particularly well-suited to absorb body excretions.

U.S. Pat. No. 4,338,371 to Dawn et al. is directed to a multi-layer absorbent product that is particularly suitable for use in environments where use of a commode is not feasible, such as for use by race car drivers, fighter plane pilots and astronauts. This product is structured so as to include a bodyside water pervious layer with a wicking layer overlaying the bodyside layer, whereby the wicking layers draw fluids away from the bodyside layer towards a container section. The container section comprises an absorbent mass sandwiched between two highly water pervious layers. The mass has the property of forming a gel when contacted with urine or some other aqueous medium.

U.K. Patent Applications Nos. 2,101,038 and 2,023,068 to Karami show a disposable product of a generally rectangular shape having a water pervious top sheet of non-woven hydrophobic fibers of polyethylene or polypropylene or a mixture thereof which permits passage of waste fluid toward the pad. A tissue wadding of hydrophobic non-woven fibers separates the pad and top sheet. A wadding lies below the pad and the water impervious backing. These patent documents state that use of a wet strength hydrophobic tissue backing prevents fluid wetback while maintaining the shape of the absorbent pad.

U.S. Pat. No. 4,050,462 to Woon et al. shows a disposable diaper with an elastically constricted crotch section. The diaper is made from material that is cut into a I-shape, which increases the cost of manufacture over a garment made from a material with straight sides. In crosssection, the Woon et al. product has a fluid permeable facing sheet, a fluid impervious backing sheet and a highly absorbent batt sandwiched between the facing and backing sheets. The fluid permeable sheet may be made of spunbonded polypropylene filaments with spot embossing, a perforated surface or a surface surfactant treatment.

U.S. Pat. No. 4,397,644 to Matthews et al. is directed to a sanitary napkin capable of rapidly transmitting viscous menstrual fluid into the absorbent portion of the napkin without cover runoff.

Thus, it becomes apparent that a need exists for an absorbent undergarment that improves the absorbent characteristics and the containment characteristics of the undergarment while still being comfortable to wear.

SUMMARY OF THE INVENTION

The present invention provides an improved absorbent undergarment having improved absorption and containment characteristics. The undergarment of the invention provides multiple absorbent layers which facilitate the formation of an adequate and comfortable crotch section when formed from a generally flat to an anatomically-conforming condition. The undergarment further provides an elasticized crotch design that also facilitates the formation of the crotch section, as well as an effective seal between the undergarment and the wearer, whereby the undergarment is comfortable to wear and has improved containment characteristics.

The present invention also provides an absorbent layer that facilitates rapid fluid transfer in an x-direction and a y-direction, and a z-direction through the absorbent layer and to absorbent layers therebeneath so that the absorption characteristics of the absorbent medium are improved.

In one form of the invention, there is provided an article for use in absorbing and containing waste comprising a generally rectangular liquid impervious backing having a peripheral edge, a generally rectangular pervious body-size liner having a peripheral edge, wherein the previous body-side liner is joined to the impervious backing near their peripheral edges. The garment further includes a generally rectangular absorbent layer between the body-side liner and the backing, and a generally rectangular pledget between said absorbent layer and said backing wherein the pledget has a width less than the width of the absorbent layer.

In another form of the invention, there is provided an article for use in the absorbing and containing of waste comprising a liquid impervious backing; a liquid pervious liner joined to the backing; an absorbent layer between the backing and the liner; and a pledget between the backing and the absorbent layer wherein the pledget is dimensioned relative to the absorbent layer so as to form a cup-shaped portion adjacent the crotch of the wearer when the garment is worn.

In another form of the invention, there is provided an article for use in absorbing and containing waste comprising a combination of a liquid impervious backing and a liquid pervious body-size liner joined near their peripheral edges, the combination being of a generally rectangular configuration and having a width between about five inches and about ten inches and a length between about twenty-three inches and about twenty-seven inches; a generally rectangular absorbent layer between the backing and the liner wherein the absorbent layer has a width between about three-fourths of an inch and four inches less than the width of the combination and a length of about 12 inches to about 27 inches; a generally rectangular pledget between the absorbent layer and the backing wherein the pledget has a length between about six inches and about fourteen inches and a width between about 30 percent and about less than 100 percent of the width of the absorbent layer; and the pledget is dimensioned relative to the absorbent layer so as to form a cup-shaped portion adjacent the crotch of the wearer when the garment is worn.

Further objects of the present invention will appear in the description hereinafter.

BRIEF DESCRIPTION OF THE DRAWINGS

The above-mentioned and other features and objects of the invention, and the manner of attaining them, will become more apparent and the invention itself will be better understood by reference to the following description of specific embodiments of the invention taken in conjunction with the accompanying drawings, wherein.

DESCRIPTION OF SPECIFIC EMBODIMENTS

Figure 1:
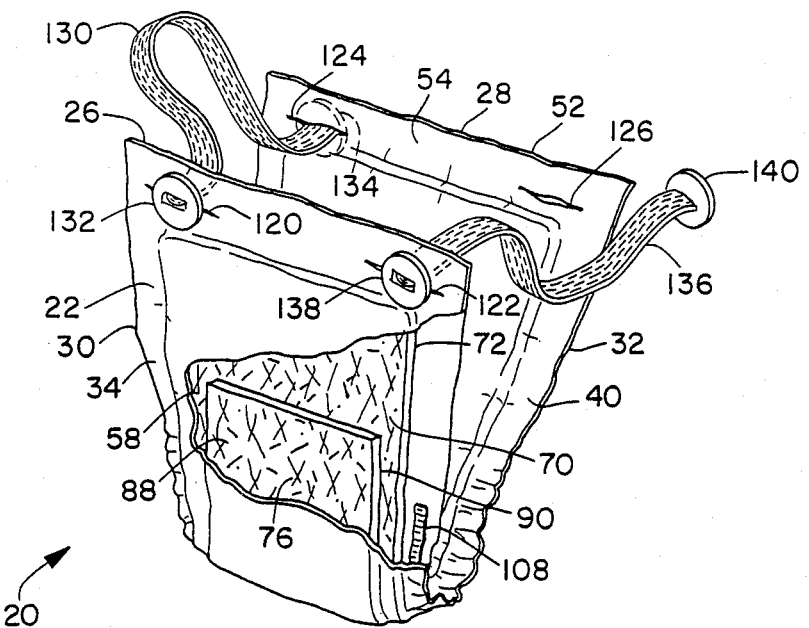
FIG. 1 is a perspective view of a specific embodiment of the invention with a portion of the liquid impervious backing removed to expose the interior structure of the embodiment.

Referring to FIGS. 1 through 4, there is illustrated one specific embodiment of the invention generally designated as 20, which presently is considered to be the best mode of practicing the invention. Undergarment 20 includes a liquid impervious backing 22 that is of a generally rectangular shape. Liquid impervious backing 22 has a peripheral edge 24 which includes a left edge 26, a right edge 28, a top edge 30 and a bottom edge 32.

Throughout this description, applicants, from time to time, make, reference to "left", "right", "top", "bottom", etc. These references are for the convenience of the reader and are to be taken with reference to the drawings as viewed by the reader. These references are not intended, and should not be taken, to limit in any fashion the scope of the invention. Further, throughout the specification, the term "generally rectangular" is used by the applicants. However, it is not intended that this term be limited to only a rectangular shape. But, instead, this term can include geometric shapes that are rectangular, oval or racetrack patterns, hourglass configurations, bilobal shapes, and in general any shape where the length is greater or less than the width.

Liquid impervious backing 22 has an exterior surface 34 that faces away from the wearer and an interior surface 36 that faces toward the wearer.

Liquid impervious backing 22 is made from about 0.75 to about 1.5 mils thick green polyethylene film. The invention contemplates the use of other materials for the liquid impervious backing 22 such as spunbond-/meltblown laminates or other polymer films. For example, impervious backing 22 can be a meltblown material made of polyethylene, polypropylene or polyolefin copolymers such as ethylene vinyl acetate, ethylene methyl acrylate, ethylene ethyl acrylate, polyvinyl chloride, Nylon and the like. Other acceptable materials include a single spunbonded layer of the above types of materials, two layers of spunbonded and meltblown materials or a three-layer material of spunbonded- meltblown-spunbonded material. Suitable foam materials may also be used, as well as materials that are both liquidimpermeable and vapor-permeable Undergarment 20 further includes a generally rectangular liquid pervious liner 40 that is of approximately the same dimension as liquid impervious backing 22. Liquid pervious liner 40 has a peripheral edge 42 comprising a left edge 44, a right edge 46, a top edge 48 and a bottom edge 50. Liquid pervious liner 40 has an exterior surface 52 that faces away from the wearer and an interior surface 54 that faces towards the wearer.

It is contemplated that the liquid pervious liner 40 can be made of any permeable nonwoven fabric alone or which is loosely bonded or sprayed to a web of natural or synthetic fibers. More specifically, the most preferable material for the liquid pervious liner 40 is a spunbonded polypropylene material having a basis weight of about 12 to about 18 grams per square meter (gsm). Liner 40 can also be a nonwoven web or sheet of polyolefin fibers, such as polypropylene, polyester, polyethylene, Rayon, chisso and the like. Liner 40 may also be a plastic film with perforations, an expanded plastic webbing material or a scrim material.

As an alternate material, liquid pervious liner 40 can be made of a carded web of polyester fibers bonded to a spunbonded polypropylene or polyethylene carrier sheet. The carded material is made up of about 20 to about 60 weight percent polypropylene or polyethylene and about 80 to about 40 weight percent polyester. The basis weight of this material can be between about 30 gsm and about 70 gsm.

Liquid impervious backing 22 and liquid pervious liner 40 are joined near their respective peripheral edges (24,42) to form what can be considered to be a container, generally designated as 74, that defines an interior volume. This interior volume contains the remaining structure of the undergarment 20, which comprises an absorbent layer 58 and a pledget 76.

The liquid impervious backing 22 and liquid pervious liner 40 have essentially the same width and length. The width of backing 22 and liner 40 ranges between about 5 inches (12.7 cm) and about 10 inches (25.4 cm). The length of backing 22 and liner 40 ranges between about 23 inches (58.4 cm) and about 27 inches (68.6 cm). In the specific embodiment of the invention as illustrated in FIGS. 1-4, the width of the backing and liner is about 8.625 inches (21.9 cm), and the length is about 25 inches (63.5 cm).

The absorbent layer 58 is of a generally rectangular shape and includes a peripheral edge 60 comprised of a left edge 62, a right edge 64, a top edge 66 and a bottom edge 68. Absorbent layer 58 has an exterior surface 70 that faces away from the wearer, and an interior surface 72 that faces towards the wearer.

Absorbent layer 58 is most preferably made from a blend of fibers comprising about 15 to about 30 weight percent polypropylene fibers and about 85 to about 70 weight percent wood pulp fluff fibers and having a basis weight of 80 to about 250 gsm. Absorbent layer 58 may be formed on a tissue or a spunbonded carrier sheet, or may be formed without a carrier sheet. It is contemplated that the absorbent layer 58 can also be made from a blend of fibers comprising between about 10 weight percent and about 90 weight percent polypropylene or polyethlene fibers and between about 90 weight percent and about 10 weight percent wood pulp fluff fibers. The absorbent layer could also be made from 100 weight percent wood pulp fluff fiber. The basis weight can range between about 80 gsm and about 500 gsm. Absorbent layer 58 can also be a batt of meltblown fibers such as polypropylene, polyethylene, polyester and the like, and may also be a bonded carded web of synthetic or natural fibers, a composite of meltblown fibers of polypropylene, polyethlene, and polyester mixed with a cellulosic material, or any other suitable absorbent material.

Absorbent layer 58 provides the feature of being able to transport liquid in what can be characterized as in an x- and y direction and in a z-direction. The transport of fluid in the z-direction is movement of a wicking nature where the fluid moves away from the body of the wearer. The transport of fluid in the x-direction and y-direction is movement of fluid along the length and width of the absorbent layer. As can be appreciated, the movement of fluid both away from the wearer and along the length and width of the absorbent layer results in an increase in the utilization of the area of the absorbent layer since the fluid moves towards the distal ends of the absorbent layer, and the result is an improvement of the absorption characteristics of the absorbent layer.

Figure 2:
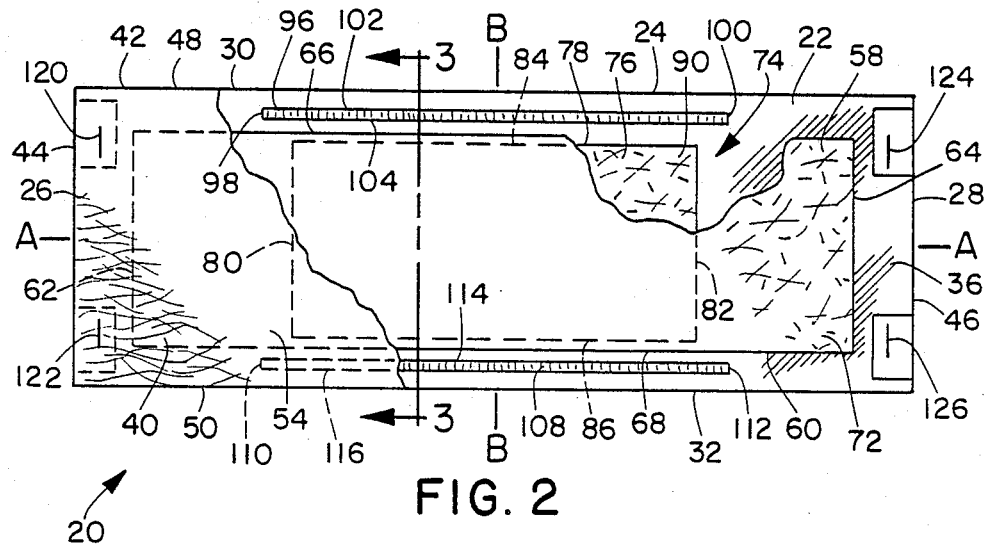
FIG. 2 is a plan view of the specific embodiment of FIG. 1 in an extended condition with the liquid pervious liner facing the viewer, and a portion of the liquid pervious liner and a portion of the absorbent layer removed.
Figure 3:
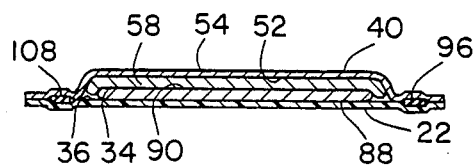
FIG. 3 is a cross-sectional view of the specific embodiment of FIG. 2 taken along section line 3—3 of FIG. 2.

As illustrated in FIG. 2, the absorbent layer 58 has a width that is measured between the top and bottom edges 66,68 thereof. Absorbent layer 58 has a length that is measured between the left and right edges 62,64 thereof. The width and length of the absorbent layer 58 are each less than the corresponding width and length of the container 74 comprised of the backing 22 and the liner 40. The width of container 74 is measured between the top and bottom edges thereof, and the length of the container 74 is measured between the left and right edges thereof.

More specifically, the width of the absorbent layer 58 is between about 60 percent and about 85 percent of the width of the container 74 comprised of the impervious backing 22 and pervious liner 40. The length of the absorbent layer 58 is between about 40 percent and 100 percent of the length of the container 74 comprised of the impervious backing 22 and the pervious liner 40.

In the specific embodiment, the absorbent layer 58 has a length equal to about 21.5 inches (54.6 cm), and a width equal to about 6 inches (15.2 cm). The width of the absorbent layer can vary, but is typically between about 0.75 inches (1.9 cm) and about 4 inches (10.1 cm) narrower than the width of the impervious backing.

Absorbent layer 58 is positioned so as to be symmetrical about the central longitudinal axis A—A of the garment 20 and the central transverse axis B—B of the garment 20. In other words, the top and bottom edges 66, 68 of the absorbent layer 58 are equi-distant from the top and bottom edges 48, 50 of the liquid pervious liner 40, respectively; and the left and right edges 62, 64 of the absorbent layer 58 are equi-distant from the left and right edges 44, 46 of the liquid pervious liner 40, respectively.

The pledget 76 is of a generally rectangular shape and has a peripheral edge 78 with a left edge 80, a right edge 82, a top edge 84 and a bottom edge 86. Pledget 76 has an exterior surface 88 facing away from the wearer and an interior surface 90 facing towards the wearer. The pledget 76 is dimensioned relative to the absorbent layer 58 such that its width and length are each less than the width and length of the absorbent layer 58, respectively. In this regard, the length of the pledget 76 is measured along the left and right edges 80, 82 thereof and the width of the pledget 76 is measured along the top and bottom edges 84, 86 thereof. The length of the absorbent layer 58 is measured along the left and right edges 62, 64 and the width of the absorbent layer 58 is measured along the top and bottom edges 66, 68.

Pledget 76 is most preferably made from a blend of fibers comprising about 15 to about 30 weight percent polypropylene or polyethylene fibers and about 85 to about 70 weight percent wood pulp fluff fibers, and has a basis weight of about 100 to about 525 gsm. In addition, a superabsorbent is added in an amount of about 10 to about 100 gsm. Pledget 76 may be formed on a tissue or a spunbonded carrier sheet, or may be formed without a carrier sheet.

Pledget 76 of the specific embodiment has a width equal to about 5.75 inches (14.6 cm) and a length equal to about 12 inches (30.5 cm). It is contemplated that pledget 76 can have a width between about 3 inches (7.6 cm) and about 8.5 inches (21.6 cm), and a length between about 6 inches (15.2 cm) and about 14 inches (35.6 cm). Pledget 76 has a dry thickness equal to about 2.63 mm to about 17.5 mm.

Pledget 76 is illustrated in the drawings to have a dry thickness that is approximately equal to the dry thickness of the absorbent layer 58. However, it should be appreciated that the pledget and absorbent layer can be of different thicknesses. For example, the pledget can be from about one-half to about four time the thickness of the absorbent layer.

Pledget 76 is illustrated in FIG. 2 as being positioned so as to be symmetrical about the central longitudinal and transverse axes A—A, B—B, respectively, of the garment 20. When in this position, the left and right edges 80, 82 of pledget 76 are equi-distant from the left and right edges 44, 46 of the liquid pervious liner 40, respectively, and the top and bottom edges 84, 86 of pledget 76 are equi-distant from the top and bottom edges 48, 50 of the liquid pervious liner 40, respectively. Further, when in this position, the absorbent layer 58 extends past the peripheral edge of the first pledget.

Pledget 76 can, however, be positioned so that either the left or right edge 80, 82 is no less than 2 inches (5.1 cm) from its respective left or right edge 44, 46 of the liquid pervious liner 40 while still being symmetrical about the central longitudinal axis A—A. In other words, the pledget 76 can be asymmetrical about the transverse axis B—B.

An elongate elastic band 96 has a left edge 98, a right edge 100, a top edge 102 and a bottom edge 104. Elastic band 96 is affixed adjacent the top edge 48 of the liquid pervious liner 40 so as to be spaced inwardly therefrom. Elastic band 96 is positioned so that the left edge 98 and the right edge 100 are equi-distant from their respective left and right edges 44, 46 of the liquid pervious liner 40. However, elastic band 96 can be positioned other than in an equi-distant arrangement relative to their edges 98, 100 and edges 44, 46.

A second elongate elastic band 108 has a left edge 110, a right edge 112, a top edge 114 and a bottom edge 116. Elastic band 108 is affixed to the liquid pervious liner 40 so as to be adjacent to the bottom edge 50 thereof, and is spaced inwardly of the bottom edge 50. Elastic band 108 is positioned so that its left edge 110 and right edge 112 are spaced equi-distant from their respective left and right edges 44, 46 of the liquid pervious liner 40. Band 108 can also be positioned other than in an equi-distant arrangement.

In the specific embodiment, the elastic bands 96, 108 are made of urethane. However, it is contemplated that elastic band 96, 108 can be made of natural rubber or other synthetic elastic material.

When stretched for adherence to the garment, the elastic bands have a length of about 14 inches (35.6 cm) and a width of about 0.42 inches (1.06 cm). When the elastic bands relax, they each are of a length equal to about 16.5 cm and a width of about 1.27 cm.

A pair of slits 120, 122 are contained in the container 74 comprised of the liquid pervious liner 40 and the liquid impervious backing 22 adjacent the left edges 44, 26 thereof, respectively. Another pair of slits 124, 126 is contained in the container 74 comprised of the liquid pervious liner and liquid impervious backing adjacent the right edges 46, 28 thereof, respectively. A strap 130 having a retainer 132, 134 at each opposite end extends between slits 120 and 124. Another strap 136 having a retainer 138, 140 at each opposite end extends between slits 122 and 126. This support system is described in issued U.S. Pat. No. 4,315,508 to Bolick, which is incorporated herein by reference.

Figure 4:
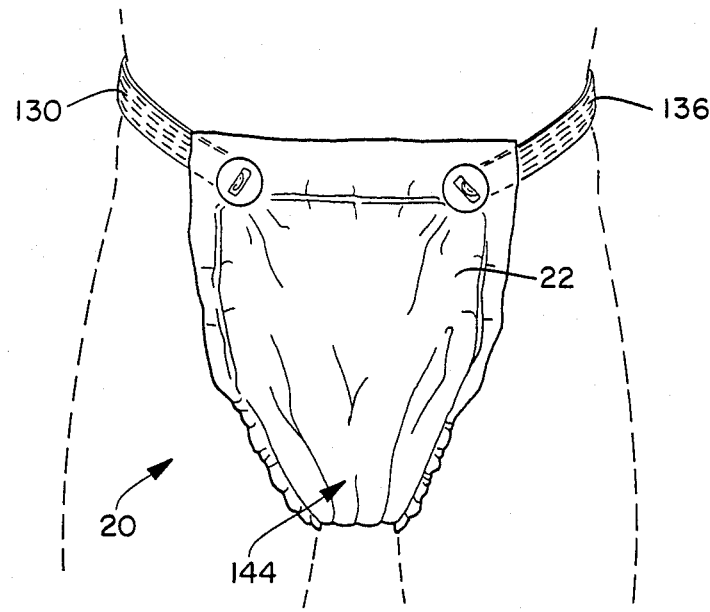
FIG. 4 is a perspective view of the specific embodiment of FIG. 1 being worn by a wearer.

When worn by a wearer, such as is illustrated in FIG. 4, the garment 20 forms a cup-shaped or anatomically-conforming portion generally designated as 144. In the specific embodiment, the formation of the cup-shaped portion is due to the presence of the pledget 76, as well as the contraction of elastic bands 96, 108. The additional thickness of absorbent material in the crotch area in the form of the pledget 76, facilitates the formation of the cup-shaped portion 144 when the garment is formed from a generally flat condition into the generally cupped condition, which is illustrated in FIGS. 1 and 4. The cup-shaped portion 144 can be formed solely due to the presence of the pledget 76.

By providing a garment that easily forms a cup-shaped portion 144 in the crotch area, the wearer does not experience any unusual discomfort. The presence of the pledget, along with the elastic bands, provides for the formation of a cup-shaped portion that creates sufficient room in the crotch area so as to not cause discomfort to the wearer.

The elastic bands 96, 108 effectively seal between the body of the wearer and the garment 20 so as to provide good containment properties in the crotch area.

As mentioned earlier, the absorbent layer 58 is made from a material that possesses properties that permits liquid movement in the x-direction and y-direction and in the z-direction. As a result, liquid is absorbed by the absorbent medium over a greater portion of its area. This feature improves the absorption characteristics of the garment. The presence of the pledget 76, which includes a superabsorbent additive, also provides increased absorbent material in the crotch area, which is the area in which additional absorbent characteristics are usually required. This coupled with the ability of the absorbent medium to be utilized to absorb liquid by its entire area results in a garment with improved absorbent properties.

Figure 5:
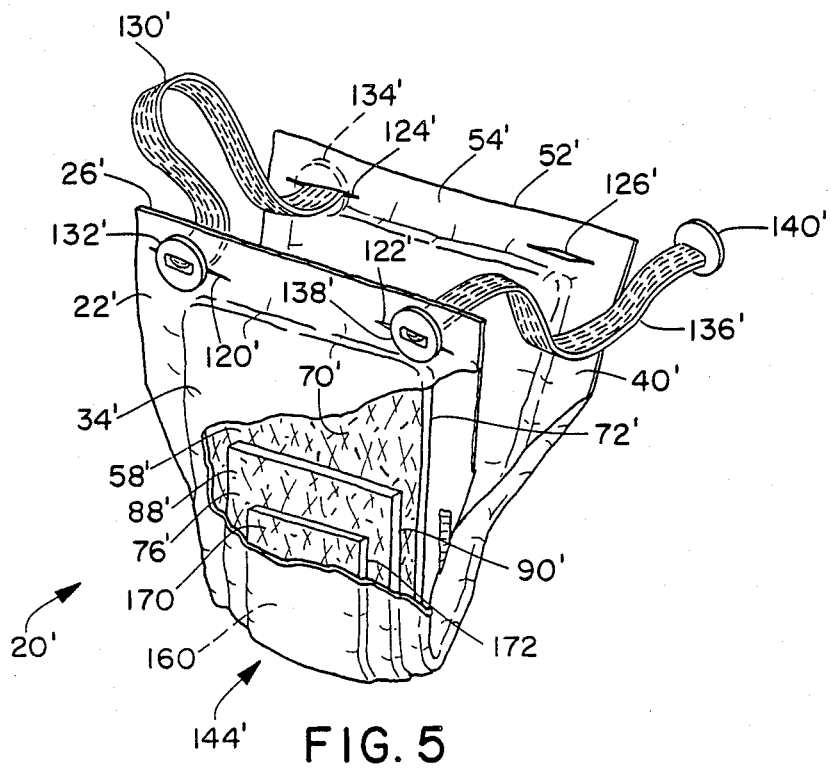
FIG. 5 is a perspective view of another specific embodiment of the invention with a portion of the liquid impervious backing removed to expose the interior structure of the specific embodiment.
Figure 6:
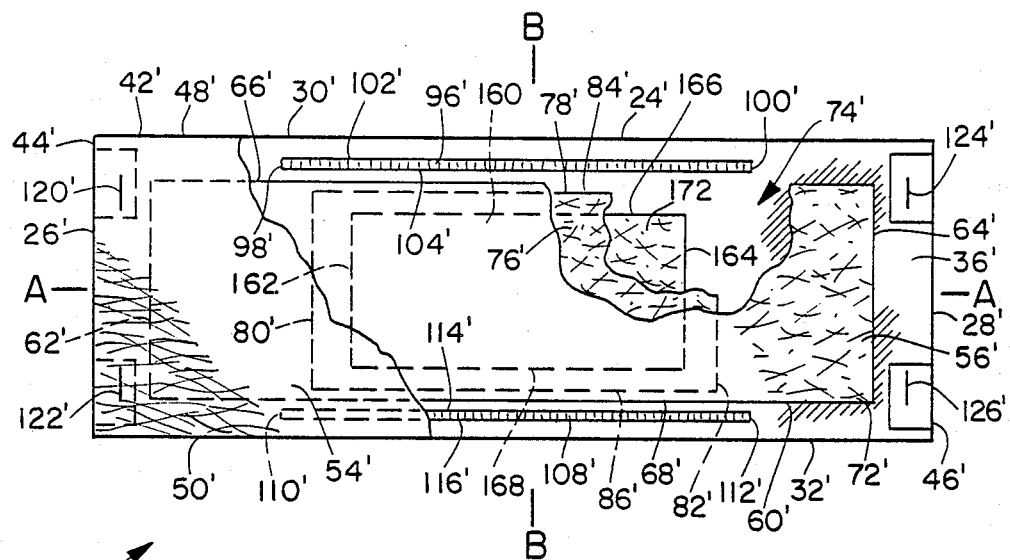
FIG. 6 is a plan view of the specific embodiment of FIG. 5 in an extended condition with the liquid pervious liner facing the viewer, and a portion of the liquid pervious liner, and the first and second absorbent layers being removed.

FIGS. 5 and 6 illustrate a second specific embodiment of the invention which is generally designated as 20'. This embodiment is constructed similar to the first specific embodiment in many respects. In this regard, those structural elements that are common between the first and second specific embodiments will be identified by the same reference numeral, except that in the case of the second embodiment, the reference numeral will be primed. Generally speaking, the structure that is common between the first and second embodiments comprises the liquid impervious backing 22, 22', the liquid pervious liner 40, 40', the absorbent layer 58, 58', and the first pledget 76, 76'

Referring to FIGS. 5 and 6, the garment 20' illustrated therein comprises a liquid impervious backing 22' and a liquid pervious liner 40' that are joined near their peripheral edges to form a container 74' that defines an interior volume. The absorbent layer 58' and the first pledget 76' are contained within the volume in much the same fashion as with the first embodiment.

Garment 20' further includes a second pledget 160 which is positioned within the interior volume of the container 74'. Second pledget 160 has a left edge 162, a right edge 164, a top edge 166 and a bottom edge 168. Second pledget 160 further includes an exterior surface 170 and an interior surface 172.

Second pledget 160 is of a generally rectangular shape, and is of a smaller width dimension, or both longitudinally and transversely more narrow, than the first pledget 76' so that the first pledget extends past the peripheral edge of the second pledget. The length of second pledget 160 can be between about 6 inches (15.2 cm) and about 27 inches (68.6 cm). The width of second pledget 160 can be between about 2 inches (5.1 cm) and about 5.5 inches (14 cm).

Second pledget 160 is illustrated as being positioned so as to be symmetrical about the central longitudinal A'—A' and transverse B'—B' axes. However, in the alternative, second pledget 160 may be positioned so that either the left or right edge 162, 164 is no less than about 1.5 inches (3.8 cm) from its respective left or right edge 44, 46 of the liquid pervious liner 40, while still being symmetrical about the central longitudinal axis A'—A' of the garment 20'.

Second pledget 160 is made from the same or different material as first pledget 76'.

The presence of the first pledget 76' and the second pledget 160 facilitates the formation of the cup-shaped or anatomically-conforming portion 144' upon the forming of the garment 20' from a generally planar condition (as illustrated in FIG. 6).

The absorbent layer 58' provides for the transfer of liquid in an x-direction and y-direction and a z-direction. As discussed above, this feature improves the absorbent properties of the absorbent medium since liquid is transferred and absorbed over most of the area of the absorbent medium. The presence of the first and second pledgets 76', 160 in the crotch area also improves the liquid absorption characteristics of the garment 20'.

As a further absorption feature, the wicking capability of the second pledget 160 is greater than that of the first pledget 76', and the wicking capability of the first pledget 76' is greater than that of the absorbent layer 58'. Liquid is easily drawn away from the body of the wearer due to this increased wicking capability.

Elastic bands 96', 108' facilitate the formation of an effective seal with the wearer.

It can thus be seen that the second embodiment provides a garment 20' which possesses improved absorbent characteristics and improved containment characteristics.

Figure 7:
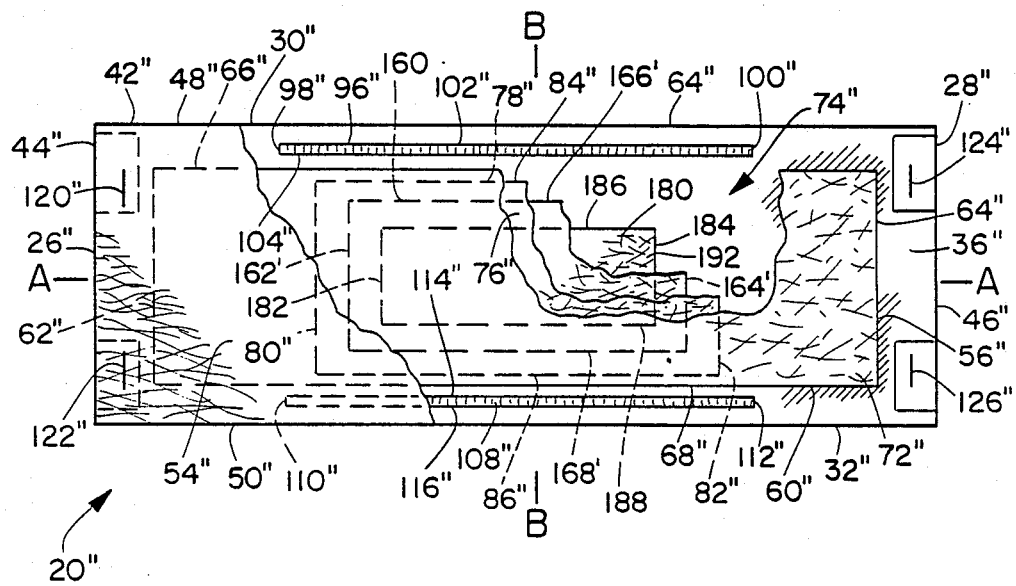
FIG. 7 is a plan view of another specific embodiment of the invention in an extended condition with the liquid pervious liner facing the viewer, and a portion of the liquid previous liner and the first, second and third absorbent layers being removed.

FIG. 7 illustrates a third specific embodiment of the invention. The third specific embodiment is constructed so as to have structure that is common with the first and second embodiments. In this regard, structural aspects of the third embodiment that are common with the first embodiment will be identified with the same reference numeral, except that the reference numeral will be double primed; and structural aspects of the third embodiment that are common with the second embodiment alone will be identified with the same reference numeral, except that the reference numeral will be primed.

The third embodiment is a garment 20" having a liquid impervious backing 22" and a liquid pervious liner 40" joined near their peripheral edges to form a container defining an interior volume. An absorbent layer 58", a first pledget 76", a second pledget 160', and a third pledget 180 are contained within this interior volume.

The liquid impervious backing 22", liquid pervious line 40", absorbent layer 58" and the first pledget 76" are essentially of the same dimension and composition as their counterparts in the first embodiment, and will not be described in detail. The second pledget 160' is constructed so as to be essentially similar in dimension and composition as the second pledget 160 of the garment 20', and will not be described in detail.

The third pledget 180 has a left edge 182, a right edge 184, a top edge 186, and a bottom edge 188. Third pledget 180 further has an exterior surface (not illustrated) and an interior surface 192. Third pledget 180 is made from the same or different materials as the first and second pledgets 76" and 160', respectively.

Third pledget 180 is of a generally rectangular shape, and is dimensioned so as to be smaller, both longitudinally and transversely, than the second pledget 160' so that the second pledget extends past the peripheral edge of the third pledget. More specifically, the third pledget has a length of between about 3 inches (7.6 cm) and about 21.5 inches (54.6 cm). The width of the third pledget 180 can be between about 1 inch (2.5 cm) and about 4.8 inches (12.2 cm).

Third pledget 180 is illustrated as being positioned so as to be symmetrical about the central longitudinal axis A"—A" and transverse B"—B" axes. However, in the alternative, third pledget 180 may be positioned so that either the left or right edge 182, 184 is no less than 1.5 inches (3.8 cm) from its respective left or right edge 44", 46" of the liquid pervious liner 40", while still being symmetrical about the central longitudinal axis A"—A" of the garment 20".

When the garment 20" is formed from the flat condition into an anatomically-conforming or cup-shaped condition, the first, second and third pledgets facilitate the formation of the cup-shaped portion (not illustrated) of the garment 20".

Absorbent layer 58" provides for the transfer of liquid in an x-direction and a y-direction and a z-direction in a fashion similar to that described above for absorbent layers 58 and 58'. This feature improves the absorbent properties of the absorbent medium since liquid is transfered and absorbed over most of the area of the absorbent medium. The presence of the first, second and third pledgets 76", 160' and 180, respectively, in the crotch area also improves the liquid absorption characteristics of the garment 20".

As an absorption feature, the wicking capability of the third pledget 180 is greater than that of the second pledget 160'. The wicking capability of the second pledget 160' is greater than that of the first pledget 76". The wicking capability of the first pledget 76" is greater than that of the absorbent layer 58". Liquid is easily drawn away from the body of the wearer due to the increased wicking capability as the layers move away from the body of the wearer.

Elastic bands 96", 108" facilitate the formation of an effective seal with the wearer.

It can thus be seen that, the third embodiment provides a garment 20″ which possesses improved absorbent characteristics and improved containment characteristics.

EXAMPLE

A specific embodiment of a garment of the invention was made in the following fashion. A piece of polyethylene sheet of about a thickness of 1.0 mils was cut to a size of about 25 inches (63.5 cm) by about 8.625 inches (21.9 cm). This sheet of polyethylene was taped to a laboratory table in an extended flat position.

A pledget is cut to a size of about 5.75 inches (14.6 cm) by about 12 inches (30.5 cm). The pledget was made from a blend of fibers comprising about 25 weight percent polypropylene fibers and about 75 weight percent wood pulp fluff fibers having a basis weight of about 440 grams per square meter, and an addition of a superabsorbent in an amount of 32 grams per square meter. Pledget has a thickness, when dry, of about 0.3 inches (0.76 cm).

The pledget is positioned on the polyethylene sheet so as to be symmetrical about the longitudinal and transverse axis of the garment. After the pledget is positioned on the polyethylene sheet, there is exposed a border of polyethylene sheet of about 1.5 inches (3.8 cm) on each longitudinal edge and a border of about 6.5 inches (16.5 cm) on each of the shorter edges.

An absorbent member is cut to a size of about 6.312 inches (16.0 cm) by about 21.5 inches (54.6 cm). The absorbent member is made from a blend of fibers comprising about 30 weight percent polypropylene fibers and about 70 weight percent wood pulp fluff fibers, and has a basis weight of about 126 grams per square meter. The absorbent member has a thickness, when dry, of about 0.154 inches (0.39 cm).

The absorbent member is positioned so as to be symmetrical about the central longitudinal and transverse axes of the garment thereby completely overlapping the pledget on all edges thereof. More specifically, the absorbent member overlaps each longitudinal edge by about 0.028 inches (0.71 cm) and overlaps each transverse edge by about 4.5 inches (11.4 cm).

Next, the liquid pervious liner was cut to a size of about 8.625 inches (21.9 cm) by about 25 inches (63.5 cm). The liquid pervious liner was made of a spunbonded polypropylene material having a basis weight of about 0.6 oz./yd$^2$ attached to the liquid impervious polyethylene backing near the peripheral edges thereof The pad was cut loose from the laboratory table. After being cut free from the laboratory table, the garment was shortened by the elastic which attempted to return to its original length. The length of the garment after shortening was about 18 inches. This length is measured after laying the pad flat and weighting the elastic portion with a book of about 2.5 pounds and about 11 inches long.

The presence of the pledget had the effect of forming a cup-shaped portion in the crotch area when the garment is moved from a flat to a cupped condition. In addition, the shortening of the elastic had the effect of helping create the cup-shaped portion.

Garments formed as in this example were tested on adults and found to possess improved absorption characteristics and improved containment characteristics while being comfortable to wear.

While this invention has been described as having preferred embodiments, it will be understood that it is capable of further modifications. This application is therefore intended to cover any variations, uses, or adaptations of the invention following the general principles thereof, and including such departures from the present disclosure as come within known or customary practice in the art to which this invention pertains and fall within the limits of the appended claims.

What is claimed is:

1. An absorbent garment defining an initial expanded shape having longitudinal and transverse axes and comprising:
   a liquid-impervious backing member;
   a liquid pervious body-side liner joined to said backing member approximate a periphery of said joined liner and backing member;
   a generally rectangular absorbent positioned between said bodyside liner and said backing member in board of the periphery of said joined liner and backing member;
   elastic gathers aligned along longitudinally extending margins of the periphery, rendering said garment elastically contractible and body-conforming adjacent the crotch of a wearer; and
   a generally rectangular pledget disposed between said absorbent and said backing member, said pledget being positioned symetrically relative to the longitudinal and transverse axes of the expanded garment and dimensioned to have a length and width less than the length and width of said absorbent, wherein said pledget, said elastic gathers and said absorbent function together to form a cup-shaped portion adjacent the crotch of the wearer when said garment is worn.

2. The article of claim 1 wherein said pledget has a thickness between about one-half to about four times greater than the thickness of said absorbent layer.

3. The article of claim 1 wherein said pledget is about three times thicker than said absorbent layer.

4. The article of claim 1 wherein said pledget has a width between about 60 percent and about 85 percent of the width of said backing.

5. The article of claim 1 wherein said pledget has a width of about two-thirds of the width of said backing.

6. The article of claim 1 wherein the width of said absorbent layer is between about 60 percent and about 85 percent of the width of said backing.

7. The article of claim 1 wherein the width of said absorbent layer is about 73 percent of the width of said backing.

8. The article of claim 1 wherein the width of the pledget is between about 10 percent and about 90 percent of the width of the width of the absorbent layer.

9. The article of claim 1 wherein the length of the pledget is between about 10 percent and about 100 percent of the length of the absorbent layer.

10. The article of claim 1 wherein the length of the absorbent layer is between about 80 percent and about 100 percent of the length of the backing.

11. The article of claim 1 wherein the length of said elasticized portion when the elastic is in an extended condition is between about 25 percent and about 80 percent of the total article length.

12. The article of claim 1 wherein said absorbent layer is a coform material having a basis weight between about 80 grams per square meter and about 500 grams per square meter and made of between about 90 weight percent polypropylene or polyethylene and about 10 weight percent wood fluff fibers and about 10 weight percent polypropylene and about 90 weight percent wood fluff fibers.

13. The article of claim 12 wherein said absorbent layer has a basis weight of about 126 grams per square meter and is made of about 80 weight percent wood fluff fiber and about 20 weight percent polypropylene.

14. The article of claim 1 wherein said pledget is a coform material having a basis weight of about 100 to about 525 grams per square meter and is made of about 70 to about 85 weight percent wood pulp fluff fibers and about 30 to about 15 weight percent polypropylene or polyethylene.

15. The article of claim 14 wherein said pledget further includes a superabsorbent.

16. An absorbent garment defining an initial expanded shape having longitudinal and transverse axes and comprising:
- a liquid-impervious backing member;
- a liquid pervious liner joined to said backing member approximate a periphery of said joined liner and backing member;
- a generally planar absorbent disposed between said backing member and said liner inboard of the periphery;
- elastic gathers aligned along longitudinally extending margins of the periphery, rendering the expanded garment elastically contractible and bodyconforming adjacent the crotch of a wearer; and
- a generally planar, superabsorbent-containing pledget disposed between said backing member and said absorbent, said pledget being positioned symetrically relative to the longitudinal and transverse axes of the expanded garment and having a length and width less than the length and width of said absorbent wherein said pledget, said absorbent and said elastic gathers function together to form a cup-shaped portion adjacent the crotch of the wearer when said garment is worn.

17. The garment of claim 16 further including a second pledget between said backing and said first pledget.

18. The garment of claim 17 wherein said second pledget is generally planar and has a peripheral edge, and said first pledget extends past the peripheral edge of said second pledget.

19. The garment of claim 18 wherein said second pledget is dimensioned so as to facilitate the formation of the cup-shaped portion when the garment is worn.

20. The garment of claim 19 further including a third pledget between said backing and said second pledget, and said third pledget is generally planar and has a peripheral edge, and said second pledget extending past the peripheral edge of said third pledget.

21. The garment of claim 20 wherein said third pledget is dimensioned so as to facilitate the formation of the cupshaped portion when the garment is worn.

22. An absorbent garment defining an initial expanded shape having longitudinal and transverse axes and comprising:
- a combination of a liquid impervious backing member and a liquid pervious body-side liner joined together approximate a periphery of said joined liner and backing member, said combination being of a generally rectangular configuration and having a width between about 5 inches and 10 inches and a length between about 23 inches and 25 inches;
- a generally rectangular absorbent positioned between said backing member and said liner inboard of the periphery and having a width between about 0.75 inch and 4 inches less than the width of said combination, said absorbent having a length of at least about 21.5 inches;
- elastic gathers aligned along longitudinally extending margins of the periphery, rendering said garment elastically contractible and bodyconforming adjacent the crotch of a wearer; and
- a generally rectangular pledget disposed between said absorbent and said backing member and positioned symetrically relative to the longitudinal and transverse axes, said pledget having a length between about 6 inches and 14 inches and a width between about 30 percent and less than 100 percent of the width of said absorbent layer, wherein said pledget, said absorbent and said elastic gathers function together to form a cup-shaped portion adjacent the crotch of the wearer when said garment is worn.

23. The article of claim 22 wherein said absorbent layer comprises wood pulp fluff fibers and polypropylene.

24. The article of claim 22 wherein said pledget comprises wood pulp fluff fibers, polypropylene and a superabsorbent.

25. The garment of claim 22 wherein said pledget contains superabsorbent.

* * * * *